US006989265B2

(12) United States Patent
Blattner et al.

(10) Patent No.: US 6,989,265 B2
(45) Date of Patent: Jan. 24, 2006

(54) BACTERIA WITH REDUCED GENOME

(75) Inventors: Frederick R. Blattner, Madison, WI (US); Gyorgy Posfai, Szeged (HU); Christopher D. Herring, Madison, WI (US); Guy Plunkett, III, Madison, WI (US); Jeremy D. Glasner, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 283 days.

(21) Appl. No.: 10/057,582

(22) Filed: Jan. 23, 2002

(65) Prior Publication Data
US 2003/0138937 A1 Jul. 24, 2003

(51) Int. Cl.
*C12N 1/20* (2006.01)

(52) U.S. Cl. .................................. 435/252.8

(58) Field of Classification Search ................ 435/243, 435/252.1, 252.5, 252.6, 252.8, 252.7, 252.9, 435/253.1, 253.2, 253.3, 253.4, 253.5
See application file for complete search history.

(56) References Cited

U.S. PATENT DOCUMENTS

| | | |
|---|---|---|
| 5,578,464 A | 11/1996 | Lunn et al. |
| 5,747,662 A | 5/1998 | Simmons et al. |
| 5,824,502 A | 10/1998 | Honjo et al. |
| 5,962,327 A | 10/1999 | Dujon et al. |
| 6,015,709 A | 1/2000 | Natesan |
| 6,022,952 A | 2/2000 | Weiner et al. |
| 6,117,680 A | 9/2000 | Natesan et al. |
| 6,238,924 B1 | 5/2001 | Dujon et al. |
| 6,335,178 B1 | 1/2002 | Weiner et al. |
| 6,372,476 B1 | 4/2002 | Belguith et al. |
| 6,410,273 B1 | 6/2002 | Crouzet et al. |
| 6,509,156 B1 | 1/2003 | Stewart et al. |

FOREIGN PATENT DOCUMENTS

| | | |
|---|---|---|
| EP | 0177343 | 4/1986 |
| WO | WO 96/14408 | 5/1996 |
| WO | WO 02/14495 A2 | 2/2002 |

OTHER PUBLICATIONS

Smalley et al., Trends in Microbiology, vol. 11, No. 1, pp. 6-8, 2003.*
Balbas (2001). Understanding the art of producing protein and non-protein molecules in *E. coli*. Molec Biotechnol 19: 251-267.
Baneyx (1999). Recombinant protein expression in *E. coli*. Current Opinion in Biotech 10: 411-421.
Berry et al. (2002). Application of metabolic engineering to improve both production and use of biotech indigo. J Indust Micro & Biotech 22: 127-133.
Blattner et al. (1997). The complete genome sequence of *Escherichia coli* K 12. Science 277:1453-74.
Blaudeck et al. (2001). Specificity of single peptide recognition in TAT-dependent bacterial protein translocation. J. Bacteriology 183:604-610.
Court et al. (2002). Genetic engineering using homologous recombination. Annu. Rev. Genet. 36: 361-88.
Danese et al. (1998). Targeting and assembly of periplasmic and outer-membrane proteins in *Escherichia coli*. Annu. Rev. Genet. 32:59-94.
Datsenko et al (2000). One-step inactivation of chromosomal genes in *Escherichia coli* K-12 using PCR products. Proc. Natl. Acad. Sci. 97:6640-6649.
Degryse (1995). Evaluation of *Escherichia coli* recBC sbcBC mutants for cloning by recombination in vivo. J. Biotechnology 39: 181-187.
DeLisa et al. (2001). Quorum sensing via AI-2 commumicates the metabolic burden associated with heterologous protein production in *E. coli*. Biotech Bioeng 75(4): 439-450.
Fekkes et al. (1999). Protein targeting to the bacterial cytoplasmic membrane. Microbiol. Mol. Biol. Rev. 63:161-193.
Gill et al. (2000). A comparative study of global stress gene regulation in response to overexpression of recombinant proteins in *E.coli*. Metabolic Engineering 2: 178-189.
Hanahan et al. (1983). Studies on transformation of *Escherichia coli* with plasmids. J. Mol. Biol. 166(4):557-580.
Hannig (1998). Strategies for optimizing heterologous protein expression in *Escherichia coli*. Trends Biotechnol. 16(2):54-60.
Hayashi et al (2001). Construction of a genetic linkage map of the model legume Lotus japonicus using an intraspecific F2 population. DNA Research 8: 11-22.
Hockney (1994). Recent developments in heterologous protein production in *Escherichia coli*. Trends Biotechnol. 12(11):456-632.

(Continued)

*Primary Examiner*—Terry McKelvey
*Assistant Examiner*—Nancy Vogel
(74) *Attorney, Agent, or Firm*—Fulbright & Jaworski, LLP

(57) ABSTRACT

The present invention provides a bacterium having a genome that is genetically engineered to be at least 2 to 14% smaller than the genome of its native parent strain. A bacterium with a smaller genome can produce a commercial product more efficiently. The present invention also provides methods for deleting genes and other DNA sequences from a bacterial genome. The methods provide precise deletions and seldom introduces mutations to the genomic DNA sequences around the deletion sites. Thus, the methods can be used to generate a series of deletions in a bacterium without increasing the possibility of undesired homologous recombination within the genome. In addition, some of the methods provided by the present invention can also be used for replacing a region of a bacterial genome with a desired DNA sequence.

6 Claims, 8 Drawing Sheets

OTHER PUBLICATIONS

Hynds et al. (1998). The sec-independent twin-arginine translocation system can transport both tightly folded and malfolded proteins across the thylakoid membrane. J. Biol. Chem. 273:34868-34874.

Kitamura (1995). DNA sequence changes in mutations in the ton B gene on the chromosome of *Escherichia coli* K-12: insertion elements dominate the spontaneous spectra. Jpn J Genet 70: 35-46.

Kolisnychenko et al. (2002). Engineering a reduced *Escherichia coli* genome. Genome Research 12:640-647.

Koob et al.. Minimizing the genome of *Escherichia coli*. Ann. N.Y. Acad. Science.

Koonin (2000). How many genes can make a cell: The minimal-gene-set concept. Ann Rev Genom Hum Genet 1: 99-116.

Lee (1996). High cell-density culture of *Escherichia coli*. TIBTECH 14:98-103.

Murphy (1998). Use of bacteriophage λ recombination functions to promote gene replacement in *Escherichia coli*. J. Bacteriol. 180: 2063-2071.

Muyrers et al. (1999). Rapid modification of bacterial artificial chromosomes by ET-recombination. Nucl. Acids. Res. 27: 1555-1557.

Neidhardt et al. (1974). Culture medium for Enterobacteria. J. Bacteriol. 119:736-747.

Oliner et al. (1993). In vivo cloning of PCR products in *E. coli*. Nucleic Acids Res. 2(22): 5192-7.

Otto et al. (2002). Surface sensing and adhesion of *E.coli* controlled by the Cpx-signaling pathway. Proc. Nat. Acad. Sci. US 99(4): 2287-2292.

Perna et al. (2001). Genome sequence of enterohaemorrhagic *Escherichia coli* O157:H7. Nature 409:529-533.

Perna et al. (2002). The genomes of *Escherichia coli* K-12 and pathogenic *E. coli*. Pathogenic *E.coli* Paradigm for Bacterial pathogenesis, M.S. Donnenberg, Editor. Academic Press.

Pfeifer et al. (2001). Biosynthesis of complex polyketides in a metabolically engineered strain of *E. coli*. 291: 1790-1792.

Posfai et al. (1997). Versatile insertion plasmids for targeted genome manipulations in bacteria: isolation, deletion, and rescue of the pathogenicity island LEE of the *Escherichia coli* O157:H7 genome. J. Bacteriol. 179: 4426-4428.

Posfai et al. (1999). Markerless gene replacement in *Escherichia coli* stimulated by a double-strand break in the chromosome. Nucl. Acids Res. 27:4409-4415.

Pugsley (1993). The complete general secretory pathway in gram-negative bacteria. Microbiol. Rev. 57:50-108.

Reisenberg (1991). High cell density cultivation of *E.coli* at controlled specific growth rate. J. Biotech 20(1): 17-27.

Ritz et al. (2001). Roles of thiol redox pathways in bacteria. Annu Rev Microbiol 55: 21-48.

Santini et al. (1998). A novel sec-independent periplasmic protein translocation pathway in *Escherichia coli*. Embo J. 17:101-112.

Sargent et al. (1998). Overlapping functions of components of a bacterial Sec-independent protein export pathway. Embo J. 17:3640-50.

Selinger et al. (2000). RNA expression analysis using a 30 base pair resolution *Escherichia coli* genome array. Nat Biotechnol 18(12): 1262-1268.

Simmons et al. (1996). Translational level is a critical factor for secretion of heterologous proteins in *E. coli*. Nature 14: 629-634.

Sing-Gasson et al. (1999). Maskless fabrication of light-directed oligonucleotide microarrays using a digital micromirror array. Nat Biotechnol. 17(10): 974 978.

Swartz (2001). Adavances in *E. coli* production of therapeutic proteins. Curr Opinion in Biotech 12: 195-201.

Thomas et al. (2001). Export of active green fluorescent protein to the periplasm by the twin-arginine translocase (Tat) pathway in *Escherichia coli*. Mol. Micro. 39(1):47-53.

Venkatesan et al. (2001). Complete DNA Sequence and analysis of the large virulence plasmid of Shigella flexneri. Infection of Immunity 3271-3285.

Weiner et al. (1998). A novel and ubiquitous system for membrane targeting and secretion of cofactor-containing proteins. Cell 93:93-101.

Welch et al. (2002). Extensive mosaic structure revealed by the complete genome sequence of uropathogenic *Escherichia coli*. Proc. Natl. Acad. Sci. USA 99(26): 17020-17024.

Yu et al. (2000). An efficient recombination system for chromosome engineering in *Escherichia coli*. Proc. Natl. Acad. Sci. USA 97: 5978-5983.

Yu et al. (2002). Minimization of the *Escherichia coli* genome using a Tn5-targeted Cre/LoxP excision system. Nature Biotech. 20:1018-1023.

Zhang et al. (1998). A new logic for DNA engineering using recombination in *Escherichia coli*. Nature Genetics 20: 123-128.

Zhang et al. (2000). DNA cloning by homologous recombination in *Escherichia coli*. Nature Biotechnology 18: 1314-1317.

Zhang et al. (2003). Phage annealing proteins promote oligonucleotide-directed mutagenesis in *Escherichia coli* and mouse ES cells. BMC Molecular Biology 4:1.

Yu et al. (Oct. 2002), Minimization of the *Escherichia coli* genome using Tn5-targeted Cre/loxP excision system, Nature Biotechnology, vol. 20, pp. 1018-1023.

* cited by examiner

BACTERIA WITH REDUCED GENOME

STATEMENT REGARDING FEDERALLY SPONSORED RESEARCH OR DEVELOPMENT

This invention was made with United States government support awarded by the following agency:

NIH GM35682

The United States has certain rights in this invention.

CROSS-REFERENCE TO RELATED APPLICATIONS

Not applicable.

BACKGROUND OF THE INVENTION

Bacteria have been used to produce a wide range of commercial products. For example, many *Streptomyces* strains and *Bacillus* strains have been used to produce antibiotics; *Pseudomonas denitrificans* and many *Propionibacterium* strains have been used to produce vitamin B12; some other bacteria have been used to produce vitamin Riboflavin; *Brevibacterium flavum* and *Corynebacterium glutamicum* have been used to produce lysine and glutamic acid, respectively, as food additives; other bacteria have been used to produce other amino acids used as food additives; *Alcaligenes eutrophas* has been used to produce biodegradable microbial plastics; and many *Acetobacter* and *Gluconobacter* strains have been used to produce vinegar. More recently, it has become common for bacteria, such as *Escherichia coli* (*E. coli*), to be genetically engineered and used as host cells for the production of biological reagents, such as proteins and nucleic acids, in laboratory as well as industrial settings. The pharmaceutical industry supports several examples of successful products which are human proteins which are manufactured in *E. coli* cultures cultivated in a fermenter.

It is not an uncommon occurrence for normal bacterial proteins to adversely affect the production or the purification of a desired protein product from an engineered bacteria. For example, when *E. coli* bacteria are used as host cells to generate in large quantity of a desired product encoded by a gene that is introduced into the host cells by a plasmid, certain normal *E. coli* gene products can interfere with the introduction and maintenance of plasmid DNA. More significantly, because of the economies of bacterial culture in making proteins in bacteria, often the cost of purification of a recombinant protein can be more than the cost of production, and some of the natural proteins produced by the bacterial host are sensitive purification problems. Many bacterial strains produce toxins that must be purified away from the target protein being produced and some strains can produce, by coincidence, native proteins that are close in size to the target protein, thereby making size separation not available for the purification process.

Also, however, the genome of a bacteria used in a fermenter to produce a recombinant protein includes many unnecessary genes. A bacteria living in a natural environment has many condition responsive genes to provide mechanisms for surviving difficult environmental conditions of temperature, stress or lack of food source. Bacteria living in a fermentation tank do not have these problems and hence do not require these condition responsive genes. The bacterial host spends metabolic energy each multiplication cycle replicating these genes. Thus the unnecessary genes and the unneeded proteins, produced by a bacterial host used for production of recombinant protein, simply represent lack of efficiencies in the system that could be improved upon.

It is not terribly difficult to make deletions in the genome of a microorganism. One can perform random deletion studies in organisms by simply deleting genomic regions to study what traits of the organism are lost by the deleted genes. It is more difficult, however, to make targeted deletions of specific regions of genomic DNA and more difficult still if one of the objectives of the method is to leave no inserted DNA, here termed a "scar," behind in the organism after the deletion. If regions of inserted DNA, i.e. scars, are left behind after a genomic deletion procedure, those regions can be the locations for unwanted recombination events that could excise from the genome regions that are desirable or engender genome rearrangements. Since in building a series of multiple deletions, scars left behind in previous steps could become artifactual targets for succeeding steps of deletion. This is especially so when the method is used repeatedly to generate a series of deletions from the genome. In other words, the organism becomes by the deletion process genetically unstable if inserted DNA is left behind.

BRIEF SUMMARY OF THE INVENTION

The present invention provides a bacterium having a genome that is genetically engineered to be at least two percent (2%) to fifteen percent (15%) smaller than the genome of its native parent strain. When used to produce a product, a bacterium with a smaller genome can have one or more of the following advantages. One, the production process can be more efficient either in terms of resource consumption or in terms of production speed, or both. Two, the product purification process can be simplified or purer products can be made. Three, a product that cannot be produced before due to native protein interference can be produced.

To make a bacterium with a smaller genome, genes and other DNA sequences that are not required for cell survival and protein production in culture can be deleted.

The present invention also provides methods for targeted deletion of genes and other DNA sequences from a bacterial genome without leaving any residual DNA from the manipulation. Since the methods of the present invention seldom introduce mutations into the genomic DNA sequences around deletion sites, the methods can be used to generate a series of deletions in a bacterium without increasing the possibility of undesired homologous recombination within the genome. Some of these methods are also useful for similar deletions in higher organisms.

The first method is linear DNA-based. To perform the process, first, a linear DNA construct is provided in a bacterium and a region of the bacterial genome is replaced by the linear DNA construct through homologous recombination aided by a system resided in the bacterium that can increase the frequency of homologous recombination. Next, a separate gene previously introduced into the bacterium expresses a sequence-specific nuclease to cut the bacterial genome at a unique recognition site located on the linear DNA construct. Then, a DNA sequence engineered into one end of the linear DNA construct undergoes homologous recombination with a similar genomic DNA sequence located close to the other end of the linear DNA construct. The net result is a precise deletion of a region of the genome.

The second method is also linear DNA-based. Two DNA sequences, one of which is identical to a sequence that flanks one end of a bacterial genome region to be deleted and the other of which is identical to a sequence that flanks the other end of the bacterial genome region to be deleted, are engineered into a vector in which the two sequences are located next to each other. At least one sequence-specific nuclease recognition site is also engineered into the vector on one side of the two sequences. The vector is introduced into a bacterium and a linear DNA is generated inside the bacterium by expressing inside the bacterium a nuclease that recognizes the sequence-specific nuclease recognition site and cuts the vector therein. The linear DNA undergoes homologous recombination with the bacterial genome aided by a system resided in the bacterium to increase the frequency of homologous recombination. A bacterium with a targeted deletion in its genome is thus produced.

The second method described above can also be used to replace a selected region of a bacterial genome with a desired DNA sequence. In this case, a desired DNA sequence that can undergo homologous recombination with and hence replace the selected region is engineered into the vector. All other aspects are the same as for deleting a targeted region.

The third method is suicide plasmid-based. The specific plasmid used in this method contains an origin of replication controlled by a promoter and a selectable marker, such as an antibiotic resistance gene. To delete a targeted region of a bacterial genome, a DNA insert that contains two DNA sequences located right next to each other, one of which is identical to a sequence that flanks one end of a bacterial genome region to be deleted and the other of which is identical to a sequence that flanks the other end of the bacterial genome region, is inserted into the plasmid. The plasmid is then introduced into the bacteria and integrated into the bacterial genome. Next, the promoter is activated to induce replication from the ectopic origin introduced into the bacterial genome so that recombination events are selected. In many bacteria, the recombination events will result in a precise deletion of the targeted region of the bacterial genome and these bacteria can be identified. An alternative way to select for recombination events is to engineer a recognition site of a sequence-specific nuclease into the specific plasmid and cut the bacterial genome with the sequence-specific nuclease after the plasmid has integrated into the bacterial genome.

The suicide plasmid-based method described above can also be used to replace a selected region of a bacterial genome with a desired DNA sequence. In this case, a DNA insert that contains a desired DNA sequence that can undergo homologous recombination with and hence replace the selected region is inserted into the plasmid. All other aspects are the same as for deleting a targeted region.

Other objects, features and advantages of the invention will become apparent upon consideration of the following detailed description.

BRIEF DESCRIPTION OF THE SEVERAL
VIEWS OF THE DRAWINGS

Figure 5A:
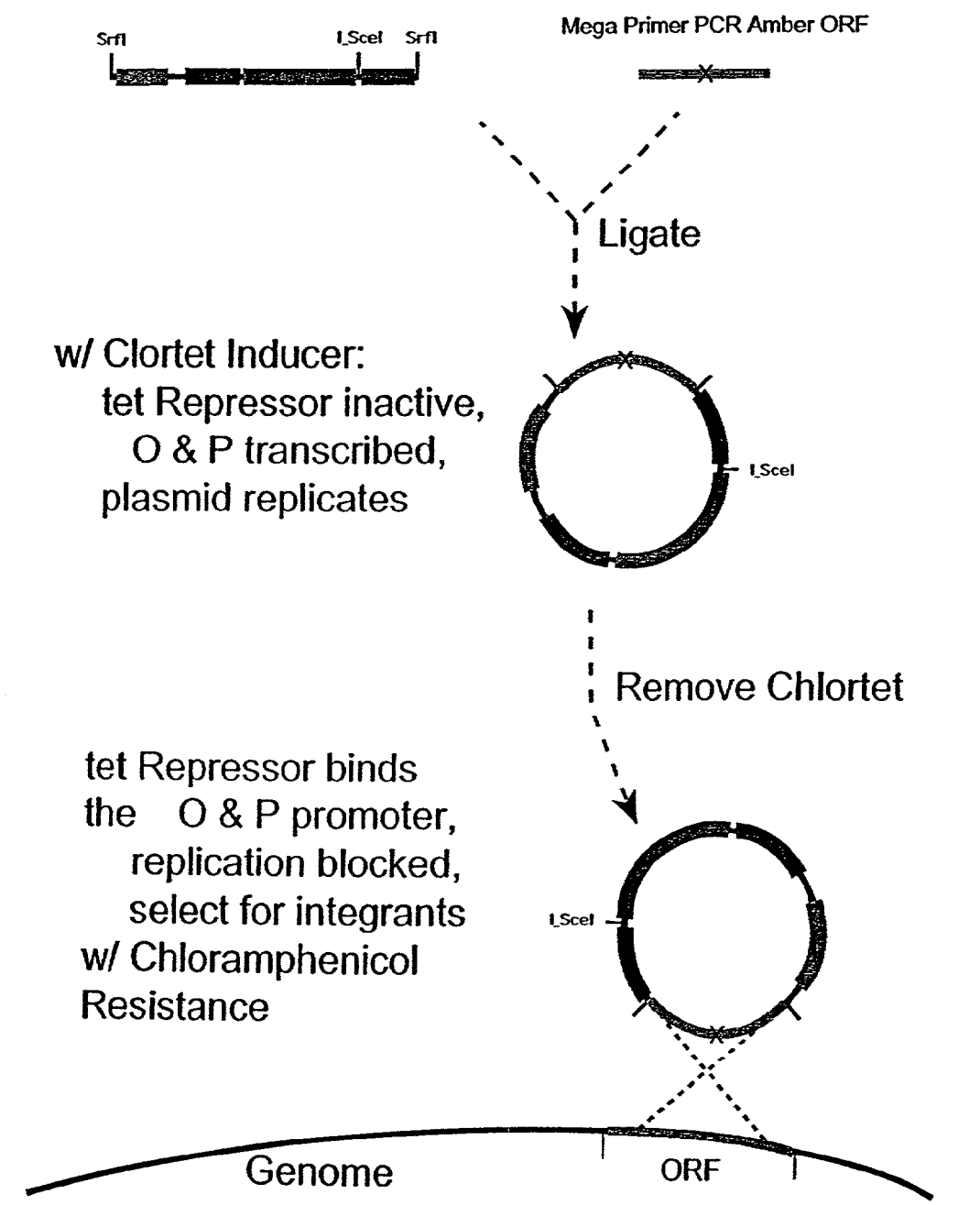
Figure 5B:
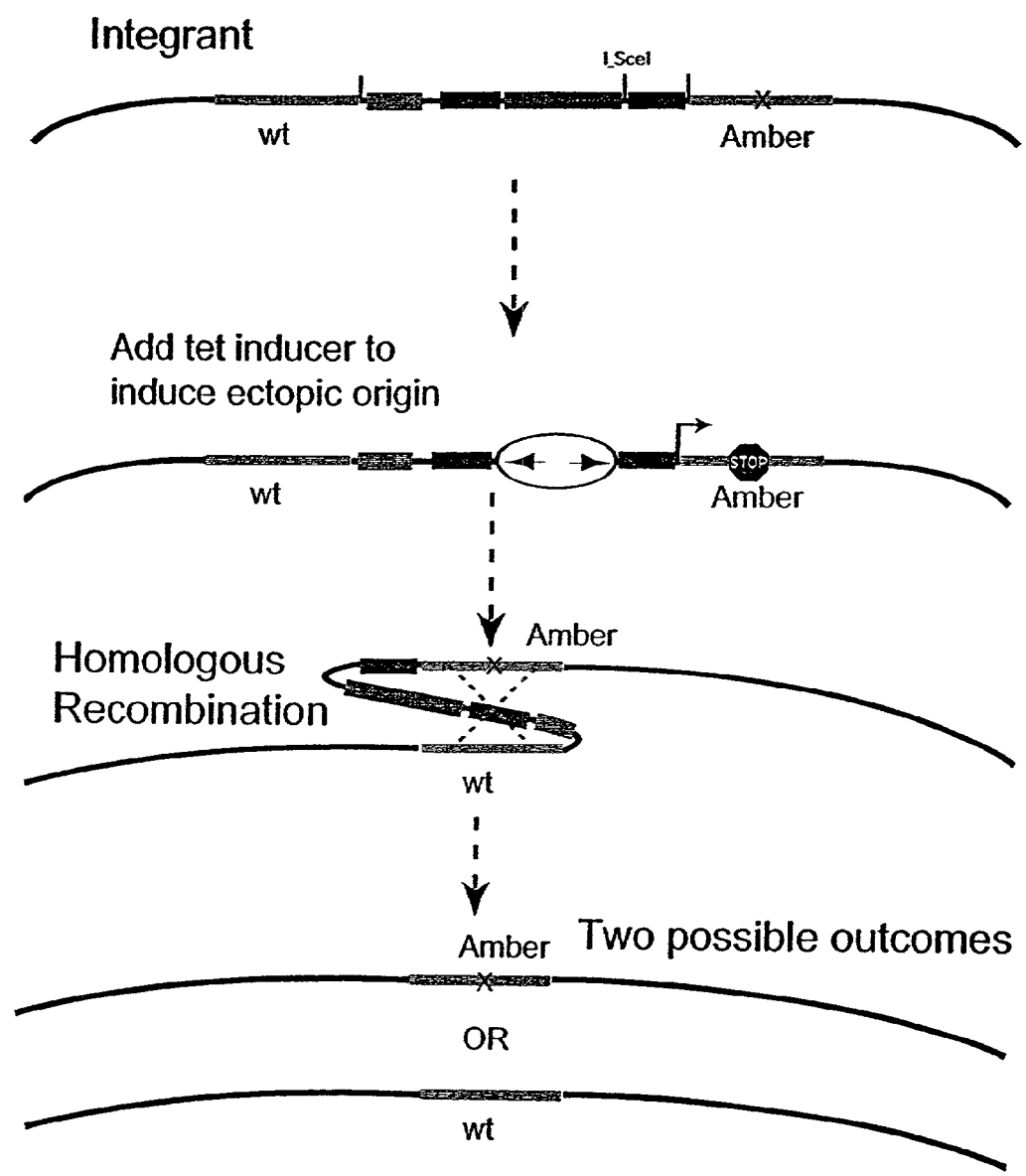
Figure 5C:
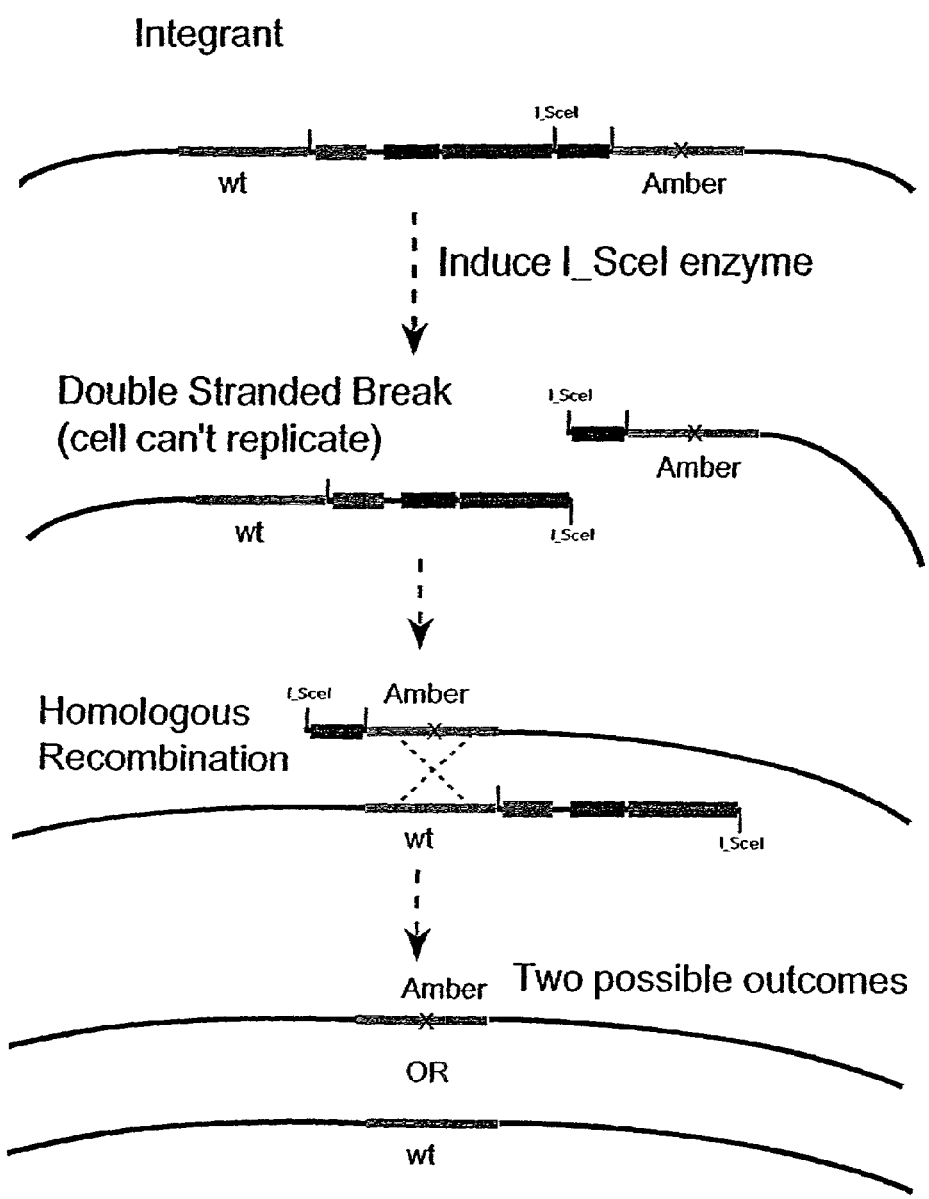

FIG. 5A-C illustrates a specific example of a suicide plasmid-based method of the present invention.

Figure 6:
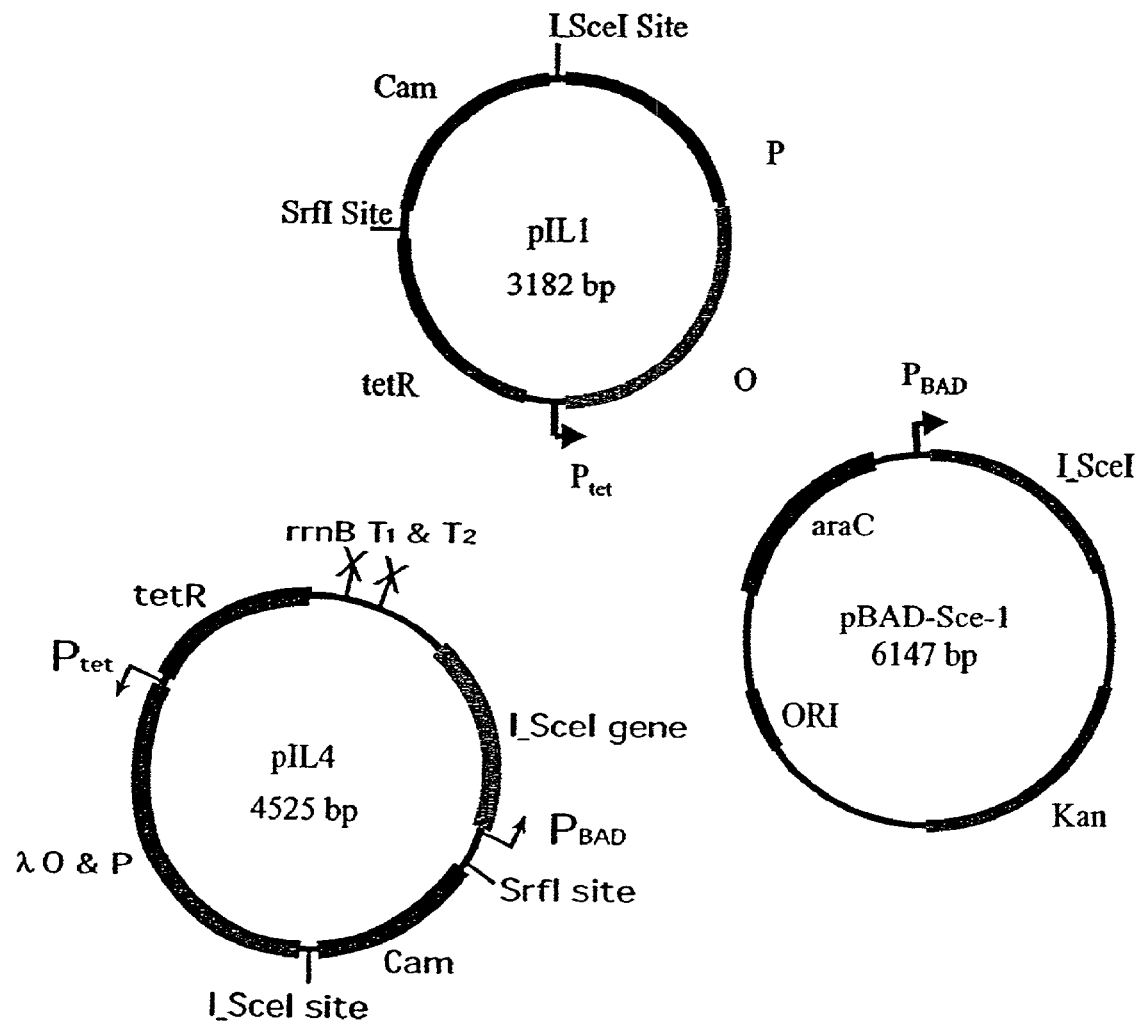

FIG. 6 shows three plasmids that can be used in the suicide plasmid-based method illustrated in FIG. 5A-C.

DETAILED DESCRIPTION OF THE
INVENTION

Bacteria in their natural environment are exposed to many conditions that are not normally experienced in standard industrial or laboratory growth, and thus carry a large number of condition-dependent, stress-induced genes or otherwise nonessential genes which may not be needed in industrial or laboratory use of the organisms. This invention began with the realization that much of the genetic information contained within the genome of a bacteria strain could be deleted without detrimental effect to use of bacteria cultures in processes of industrial or laboratory importance. It was recognized that a bacterium with a reduced genome might be advantageous over native strains in many industrial and laboratory applications. For example, a bacterium with a reduced genome is at least somewhat less metabolically demanding and thus can produce a desired product more efficiently. In addition, a reduced genome can lead to fewer native products and lower level of certain native proteins, allowing easier purification of a desired protein from the remaining bacterial proteins. Furthermore, some bacterial genetic sequences are associated with instabilities that can interfere with standard industrial or laboratory practices, and might entail costly and burdensome quality control procedures.

The present invention also involves several methods for deleting genomic DNA from a genome without leaving any inserted DNA behind. If one is making several sequential deletions from the single DNA molecule which makes up a bacterial genome, it is important not to leave any inserted DNA sequences behind. Such inserted sequences, if they were left behind, would be candidate sites for undesired recombination events that would delete uncharacterized and perhaps important portions of the remaining genome from the bacteria or cause other unanticipated genome rearrangements with untoward effects. Since one of the objectives of the genome reduction effort is to increase the genetic stability of the bacteria, leaving any inserted DNA behind would be contrary to the objective, and should be avoided. Thus the methods used to delete DNA from the genome become important and sophisticated.

In one aspect, the present invention relates to a bacterium having a genome that is genetically engineered to be smaller than the genome of its native parent strain. For exemplary purposes, the work described here has focused on the common laboratory and industrial bacterium *Escherichia coli*. The genome reduction work described here began with the laboratory *E. coli* strain K12, which had prior to the work described here, a genome of 4,639,221 nucleotides or base pairs. The bacterium of the present invention can have a genome that is at least two percent (2%), preferably over five percent (5%), and as much as 14% to 16%, smaller than the genome of its native parental strain. We have so far reduced the genome of *E. coli* K12 by about eight percent (8%), without disabling the bacteria from its protein production utility. The term "native parental strain" means a bacteria strain found in natural or native environment as commonly understood by the scientific community and on whose genome a series of deletions can be made to generate a bacterial strain with a smaller genome. The percentage by which a genome has become smaller after a series of deletions is calculated by dividing "the total number of base pairs deleted after all of the deletions" by "the total number of base pairs in the genome before all of the deletions" and then multiplying by 100.

Generally speaking, the types of genes, and other DNA sequences, that can be deleted are those the deletion of which does not adversely affect the rate of survival and proliferation of the bacteria under specific growth conditions. Whether a level of adverse effect is acceptable depends on a specific application. For example, a 30% reduction in proliferation rate may be acceptable for one application but not another. In addition, adverse effect of deleting a DNA sequence from the genome may be reduced by measures such as changing culture conditions. Such measures may turn an unacceptable adverse effect to an acceptable one.

Below, E. coli is used as an example to illustrate the genes and other DNA sequences that are candidates for deletion in order to generate a bacterium that can produce a desired product more efficiently. The general principles illustrated and the types of genes and other DNA sequences identified as candidates for deletion are applicable to other bacteria species or strains. It is understood that genes and other DNA sequences identified below as deletion candidates are only examples. Many other E. coli genes and other DNA sequences not identified may also be deleted without affecting cell survival and proliferation to an unacceptable level.

It is assumed in the analysis and methodology described below that the DNA sequence of the target bacterial strain is available. The full genomic sequence of several strains of E. coli is, of course, now published (for example, Blattner et al, Science, 277:1453–74, 1997; Perna et al, nature, 409, 529–533, 2001; Hayashi et al, DNA Res., 8, 11–22, 2001), as is the sequence of several other commonly used laboratory bacteria. To start the deletion process, the genome of the bacteria is analyzed to look for those sequences that represent good candidates for deletion. Of course, these techniques can also be applied to partially sequenced genomes in the genomic areas for which sequence date is available or could be determined.

In E. coli, and other bacteria as well, as well as in higher organisms, a type of DNA sequence that can be deleted includes those that in general will adversely affect the stability of the organism or of the gene products of that organism. Such elements that give rise to instability include transposable elements, insertion sequences, and other "selfish DNA" elements. For example, insertion sequence (IS) elements and their associated transposes are often found in bacterial genomes, and thus are targets for deletion. IS sequences are common in E. coli, and all of them may be deleted. For purposes of clarity in this document, we use the term IS element generically to refer to DNA elements, whether intact or defective, that can move from one point to another in the genome. An example of the detrimental effects of IS elements in science and technology is the fact that they can hop from the genome of the host E. coli into a BAC plasmid during propagation for sequencing. Many instance are found in the human genome and other sequences in the GenBank database. This artifact could be prevented by deletion from the host cells of all IS elements. For a specific application, other specific genes associated with instability may also be deleted.

Figure 1:
FIG. 1 shows positions of the genes and other DNA sequences on *E. coli* K-12 bacterial genome that were candidates for deletion as black and lighter hatched boxes on the outermost ring.

Shown in FIG. 1 is illustration of the E. coli genome, which natively, in the K12 strain, comprises 4,639,221 base pairs. FIG. 1, shows, on the inner ring, the scale of the base pair positions of the E. coli K12 genome (strain MG1655), scaled without deletions. The next ring progressively outward shows regions of the K12 genome that are missing or highly altered in a related strain O157:H7, and which are thus potentially deletable from the K12 genome. The next ring outward shows the positions of the IS elements, both complete and partial, in the native genome. The next ring moving outward shows the positions of the RHS elements A to E and flagellar and restriction regions specially targeted for deletion here. The outermost ring shows the location of the deletions actually made to the genome, as also listed in Tables 1 and 2 below. These deletions make up about 14 percent of the base pairs in the original K12 MG 1655 genome.

Another family of E. coli genes that can be deleted is the flagella gene family. Flagella are responsible for motility in bacteria. In natural environments, bacteria swim to search for nutrients. In cultured environments, bacteria motility is not important for cell survival and growth and the swimming action is metabolically very expensive, consuming over 1% of the cellular energy to no benefit. Thus, the flagella genes may be deleted in generating a bacterium with a smaller genome. Positions of flagella genes on an E. coli genome map are shown in FIG. 1 and Table 1.

Another family of E. coli genes that can be deleted is the restriction modification system and other nucleases whose products destroy foreign DNA. These genes are not important for bacterial survival and growth in culture environments. These genes can also interfere with genetic engineering by destroying plasmids introduced into a bacterium. Thus, these genes can be deleted in generating a bacterium with a smaller genome. Positions of restriction modification system genes on an E. coli genome map are shown in FIG. 1 and Table 1.

One type of E. coli DNA element, already mentioned, that can be deleted is the IS elements. IS elements are not important for bacteria survival and growth in a cultured environment and are known to interfere with genome stability. Thus, the IS elements can be deleted in generating a bacterium with a smaller genome. Positions of the IS elements on an E. coli genome map are shown in FIG. 1 and Table 1.

Another type of E. coli DNA element that can be deleted is the Rhs elements. All Rhs elements share a 3.7 Kb Rhs core, which is a large homologous repeated region (there are 5 copies in E. coli K-12) that provides a means for genome rearrangement via homologous recombination. The Rhs elements are accessory elements which largely evolved in some other background and spread to E. coli by horizontal exchange after divergence of E. coli as a species. Positions of the Rhs elements on an E. coli genome map are shown in FIG. 1 and Table 1.

One type of region in the E. coli genome that can be deleted is the non-transcribed regions because they are less likely to be important for cell survival and proliferation. Another type of regions in the E. coli genome that can be deleted is the hsd regions. The hsd regions encode for the major restriction modification gene family which has been discussed above. Positions of the non-transcribed regions and the hsd regions on an E. coli genome map are shown in FIG. 1 and Table 1.

One general method to identify additional genes and DNA sequences as deletion candidates is to compare the genome of one bacterial strain to another. Any DNA sequences that are not present in both strains are less likely to be functionally essential and thus can be used for identifying candidates for deletion. In the examples described below, the complete genomic sequences of two E. coli strains, O157:H7 EDL933 and K-12 MG1655, were compared. DNA sequences that were not found in both strains were used to identify targets for deletion. Twelve such identified targets from E. coli strain MG1655 were deleted, resulting in a bacteria strain with a genome that is about 8% smaller. The bacteria with the reduced genome are alive and grow at substantially the same rate as the native parent MG1655 strain.

One can test the consequence of deleting one or several genes or other DNA sequences from the genome. For example, after one or several genes or other DNA sequences of the genome have been deleted, one can measure the survival and proliferation rate of the resultant bacteria. Although most of the above-identified genes or other DNA sequences may be deleted without detrimental effect for purpose of producing a desired product, it is possible that the deletion of a specific gene or other DNA sequence may have an unacceptable consequence such as cell death or unacceptable level of reduction in proliferation rate. This possibility exists because of redundancies in gene functions and interactions between biological pathways. Some deletions that are viable in a strain without additional deletions will be deleterious only in combination with other deletions. The possibility exists also because of certain methods used to identify deletion candidates. For example, one method used to identify deletion candidates is to compare two E. coli strains and select genes or other DNA sequences that are not present in both strains. While the majority of these genes and other DNA sequences are not likely to be functionally essential, some of them may be important for a unique strain. Another method used to identify deletion candidates is to identify non-transcribed regions and the possibility exists that certain non-transcribed regions may be important for genome stability.

The consequence of deleting one or several genes or other DNA sequences to be tested depends on the purpose of an application. For example, when high production efficiency is the main concern, which is true for many applications, the effect of deletions on proliferation rate and medium consumption rate can be the consequence tested. In this case, the consequence tested can also be more specific as the production speed and quantity of a particular product. When eliminating native protein contamination is the main concern, fewer native proteins and lower native protein levels, or the absence of a specific native protein, can be the consequence tested.

Testing the consequence of deleting a gene or other DNA sequence is important when little is known about the gene or the DNA sequence. Though laborious, this is another viable method to identify deletion candidates in making a bacterium with a reduced genome. This method is particularly useful when candidates identified by other methods have been deleted and additional candidates are being sought.

When the consequence of deleting a gene or other DNA sequence has an effect on the viability of the bacteria under a set of conditions, one alternative to not deleting the specific gene or other DNA sequence is to determine if there are measures that can mitigate the detrimental effects. For example, if deleting lipopolysaccharide (LPS) genes results in poor survival due to more porous cellular membranes caused by the absence from the cellular membranes of the transmembrane domain of the LPS proteins, culture conditions can be changed to accommodate the more porous cellular membranes so that the bacteria lacking the LPS genes can survive just as well as the bacteria carrying the LPS genes.

Methods for deleting DNA sequences from bacterial genomes that are known to one of ordinary skill in the art can be used to generate a bacterium with a reduced genome. Examples of these methods include but are not limited to those described in Posfai, G. et al., *J. Bacteriol.* 179: 4426–4428 (1997), Muyrers, J. P. P. et al., *Nucl. Acids Res.* 27:1555–1557 (1999), Datsenko, K. A. et al., *Proc. Natl. Acad. Sci.* 97:6640–6649 (2000) and Posfai, G. et al., *Nucl. Acids Res.* 27:4409–4415 (1999), all of which are hereby incorporated by reference in their entirety. Basically, the deletion methods can be classified to those that are based on linear DNAs and those that are based on suicide plasmids. The methods disclosed in Muyrers, J. P. P. et al., *Nucl. Acids Res.* 27:1555–1557 (1999) and Datsenko, K. A. et al., *Proc. Natl. Acad. Sci.* 97:6640–6649 (2000) are linear DNA-based methods and the methods disclosed in Posfai, G. et al., *J. Bacteriol.* 179: 4426–4428 (1997) and Posfai, G. et al., *Nucl. Acids Res.* 27: 4409–4415 (1999) are suicide plasmid-based methods.

Some known methods for deleting DNA sequences from bacterial genomes introduce extraneous DNA sequences into the genome during the deletion process and thus create a potential problem of undesired homologous recombination if any of the methods is used more than once in a bacterium. To avoid this problem, scarless deletion methods are preferred. By scarless deletion, we mean a DNA sequence is precisely deleted from the genome without generating any other mutations at the deletion sites and without leaving any inserted DNA in the genome of the organism. However, due to mistakes, such as those made in PCR amplification and DNA repairing processes, one or two nucleotide changes may be introduced occasionally in scarless deletions. Described below are some novel scarless deletion methods, either linear DNA-based or suicide plasmid-based. These novel methods have been applied to E. coli strains in the examples described below. It is understood that the specific vectors and conditions used for E. coli strains in the examples can be adapted by one of ordinary skill in the art for use in other bacteria. Similar methods and plasmids can be used to similar effect in higher organisms. In some instances it may be more appropriate to modify an existing production strain rather than transfer production to the minimized genome E. coli strain.

Novel Linear DNA-Based Scarless Deletion Method I

Figure 2:
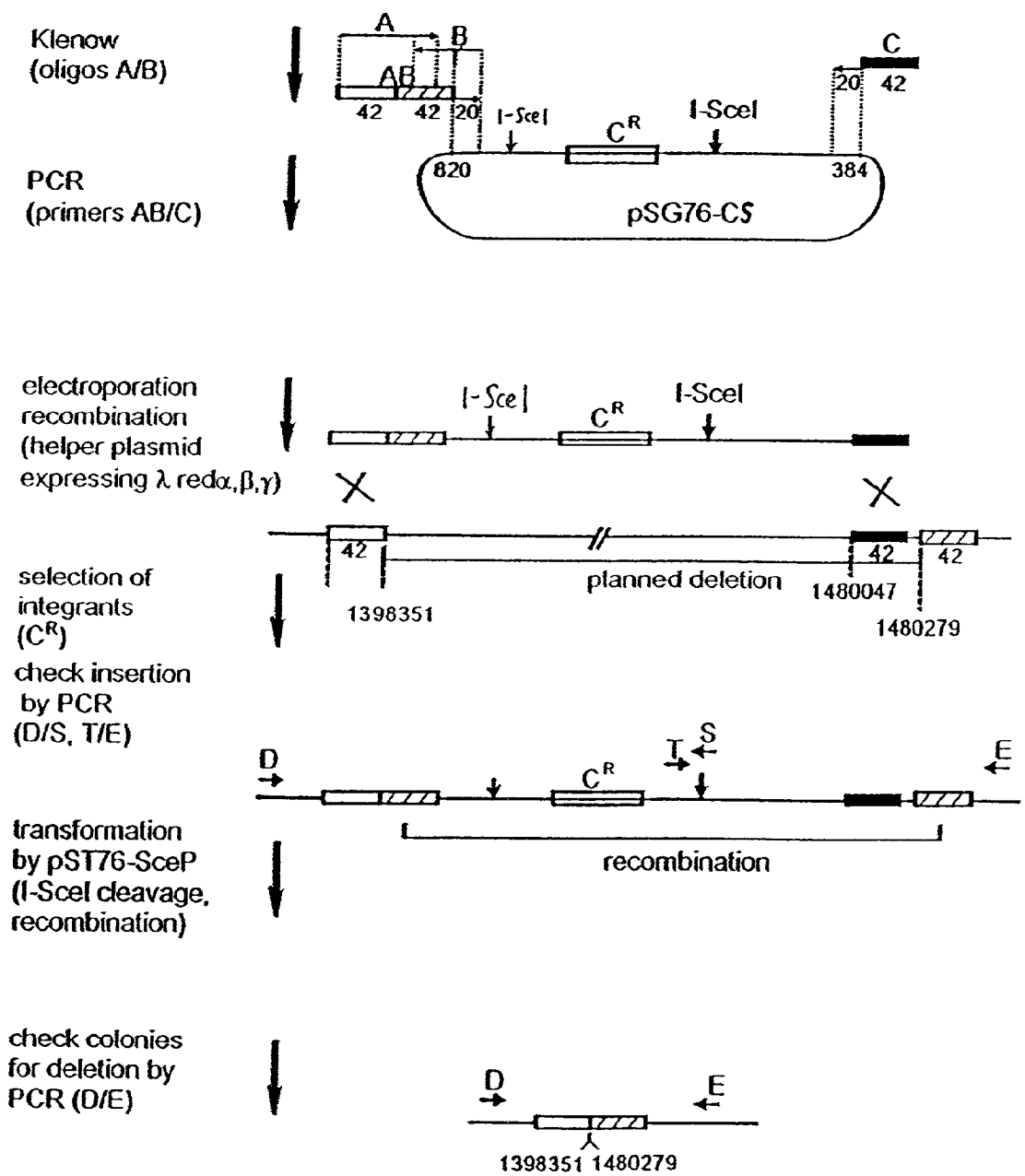
FIG. 2 illustrates a specific example of a linear DNA-based scarless genetic modification method of the present invention.

The novel DNA-based scarless deletion method of the present invention can be best understood when the following description is read in view of FIG. 2. Generally speaking, the method involves replacing a segment of the genome, marked for deletion, with an artificial DNA sequence. The artificial sequence contains one or more recognition sites for a sequence-specific nuclease such as I-SceI, which cuts at a sequence that does not occur natively anywhere in the E. coli K12 genome. Precise insertion of the linear DNA molecule into the genome is achieved by homologous recombination aided by a system that can increase the frequency of homologous recombination. When the sequence-specific nuclease is introduced into the bacteria, it cleaves the genomic DNA at the unique recognition site or sites, and only those bacteria in which a homologous recombination event has occurred will survive.

Referring specifically to FIG. 2, the plasmid pSG76-CS is used as a template to synthesize the artificial DNA insert. The artificial insertion sequence extends between the sequences designated A, B and C in FIG. 2. The $C^R$ indicates a gene for antibiotic resistance. The insert DNA is PCR amplified from the plasmid and electroporated into the E.

coli host. The insert was constructed so that the sequences A and B match sequences in the genome of the host which straddle the proposed deletion. Sequence C of the insert matches a sequence in the host genome just inside sequence B of the host genome. Then the bacteria are selected for antibiotic resistance, a selection which will be survived only by those bacteria in which a homologous recombination event occurred in which the artificial DNA inserted into the bacterial genome. This recombination event occurs between the pairs of sequences A and C. The inserted DNA sequence also includes a sequence B, now positioned at one end of the insert, which is designed to be homologous to a sequence in the genome just outside the other end of the insert, as indicated in FIG. 2. Then, after growth of the bacteria, the bacteria is transformed with a plasmid, pSTKST, which expresses the I-SceI sequence-specific nuclease. The I-SceI enzyme cuts the genome of the bacteria, and only those individuals in which a recombination event occurs will survive. 10–100% of the survivors are B to B recombination survivors, which can be identified by a screening step. The B to B recombination event deletes the entire inserted DNA from the genome, leaving nothing behind but the native sequence surrounding the deletion.

To repeat, the first step of the method involves providing a linear DNA molecule in a bacterium. The linear DNA molecule contains an artificial linear DNA sequence that has the following features: one end of the linear DNA sequence is a sequence identical to a genome sequence on the left flank of the genome region to be deleted, followed by a sequence identical to a genome sequence on the right flank of the genome region to be deleted; the other end of the linear DNA molecule is a sequence identical to a genome sequence within the genome region to be deleted; between the two ends of the linear DNA, there is a recognition site that is not present in the genome of the bacterial strain and an antibiotic selection gene. The artificial DNA sequence can be made using polymerase chain reaction (PCR) or directed DNA synthesis. A PCR template for this purpose contains the unique recognition site and the genomic DNA sequences on both ends of the artificial linear DNA sequence are part of the primers used in the PCR reaction. The PCR template can be provided by a plasmid. An example of a plasmid that can be used as a template is pSG76-C (GenBank Accession No. Y09893), which is described in Posfai, G. et al., *J. Bacteriol.* 179: 4426–4428 (1997). pSG76-CS (GenBank Accession No. AF402780), which is derived from pSG76-C, may also be used. pSG76-CS contains the chloramphenicol resistance ($Cm^R$) gene and two I-SceI sites, and was obtained by the PCR-mediated insertion of a second I-SceI recognition site into pSG76-C, downstream of the NotI site. The two I-SceI sites are in opposite direction.

An artificial or constructed DNA sequence can be provided to a bacterium by directly introducing the linear DNA molecule into the bacterium using any method known to one of ordinary skill in the art such as electroporation. In this case, a selection marker such as an antibiotic resistance gene is engineered into the artificial DNA sequence for purpose of selecting colonies containing the inserted DNA sequence later. Alternatively, a linear DNA molecule can be provided in a bacterium by transforming the bacterium with a vector carrying the artificial linear DNA sequence and generating a linear DNA molecule inside the bacterium through restriction enzyme cleavage. The restriction enzyme used should only cut on the vector but not the bacterial genome. In this case, the artificial linear DNA sequence does not have to carry a selection marker because of the higher transformation efficiency of a vector so that a bacterium with the inserted linear DNA can be screened by PCR later directly.

The second step of the scarless deletion method involves replacement of a genomic region by insertion of the artificial DNA molecule. The bacterial cells are engineered to contain a system that increases the frequency of homologous recombination. An example of such a system is the Red recombinase system. The system can be introduced into bacterial cells by a vector. The system helps the linear DNA molecule to replace a genomic region which contains the deletion target. As described in the examples below, a vector carrying a homologous recombination system that can be used in *E. coli* is pBADαβγ, which is described in Muyrers, J. P. P. et al., *Nucl. Acids Res.* 27:1555–1557 (1999). Another plasmid pKD46 described in Datsenko, K. A. et al., *Proc. Natl. Acad. Sci.* 97:6640–6649 (2000) may also be used. Other plasmids that can be used include pGPXX and pJGXX. pGPXX is derived from pBADαβγ by replacing the origin of replication in pBADαβγ with pSC101 origin of replication. pJGXX is a pSC101 plasmid that encodes the Red functions from phage 933W under tet promoter control The third step of the scarless deletion method involves removal of the inserted DNA sequence. An expression vector for a sequence-specific nuclease such as I-SceI that recognizes the unique recognition site on the inserted DNA sequence is introduced into the bacteria. The sequence-specific nuclease is then expressed and the bacterial genome is cleaved. After the cleavage, only those cells in which homologous recombination occurs resulting in a deletion of the inserted linear DNA molecule can survive. Thus, bacteria with a target DNA sequence deleted from the genome are obtained. Examples of sequence-specific nuclease expression vectors that can be used in *E. coli* include pKSUC1, pKSUC5, pSTKST, pSTAST, pKTSHa, pKTSHc, pBAD-Sce1 and pBADSce2. The sequence-specific nuclease carried by these vectors is I-SceI. pKSUC1, pKSUC5, pSTKST and pSTAST are described below in the examples.

The method described above can be used repeatedly in a bacterium to generate a series of deletions. When the expression vector for the homologous recombination system and the expression vector for the unique sequence-specific nuclease are not compatible with each other, such as the case for pBADαβγ and pKSUC1, transformation of the two vectors have to be performed for each deletion cycle. Transformation of the two vectors can be avoided in additional deletion cycles when two compatible plasmids, such as pBADαβγ and pSTKST, or pKD46 and pKSUC5, are used. An example of using two of these vectors that are compatible with each other is described in the examples below.

The above scarless deletion method can be modified to make a series of deletions on a bacterial genome more efficient (an example of which is Procedure 4 in Examples below). The first step of the modified method involves making insertions of a linear DNA molecule individually in bacterial cells, preferably wild-type bacteria cells, in a parallel fashion, resulting in a set of strains, each carrying a single insertion. This step can be carried out as described above. The second step of the modified method involves sequentially transferring individual insertions into the target cell whose genome is to be reduced. P1 transduction is an example of the methods that can be used for transferring insertions. The third step of the modified method involves recombinational removal of the inserted sequence, which can be carried out as described above.

Novel Linear DNA-Based Scarless Deletion Method II

In this novel linear DNA-based method, two DNA sequences, one of which is identical to a sequence that flanks one end of a bacterial genome region to be deleted and the other of which is identical to a sequence that flanks the other end of the bacterial genome region and oriented similarly, are engineered into a plasmid vector. The vector is herein termed the target vector. The two DNA sequences are located next to each other on the target vector. At least one recognition site for an enzyme that will only cut the target vector but not the bacterial genome is also engineered into the target vector at a location outside the two DNA sequences. The recognition site can be one for a sequence-specific nuclease such as I-SceI. The recognition site can also be one for a methylation-sensitive restriction enzyme that only cuts an unmethylated sequence. Since the recognition site, if there is any, on the bacterial genome is methylated, the restriction enzyme can only cut the target vector. The target vector is transformed into a bacterium and a linear DNA molecule is generated inside the bacterium by expressing in the bacterium the enzyme that recognizes and cuts the recognition site on the target vector. Next, a system that can increase homologous recombination is activated inside the bacterium to induce homologous recombination between the homologous sequences of the linear DNA and the bacterial genome that flank the region to be deleted. A bacterium with a targeted genome region deleted can be obtained as a result of the above homologous recombination.

This novel linear DNA-based method can also be used to replace a region of a bacterial genome with a desired DNA sequence. In this case, a desired DNA sequence that can undergo homologous recombination with the bacterial genome to replace a region on the genome is engineered into the target vector. All other aspects are the same as described above for deleting a region of the bacterial genome.

Regardless whether the method is used to delete or replace a target region in the bacterial genome, a marker gene for selecting incorporation of DNA carried on the target vector into the bacterial genome is not necessary due to the high incorporation efficiency. Simply screening 30–100 colonies by PCR usually allows the identification of a clone with desired modification in the bacterial genome.

Figure 3:
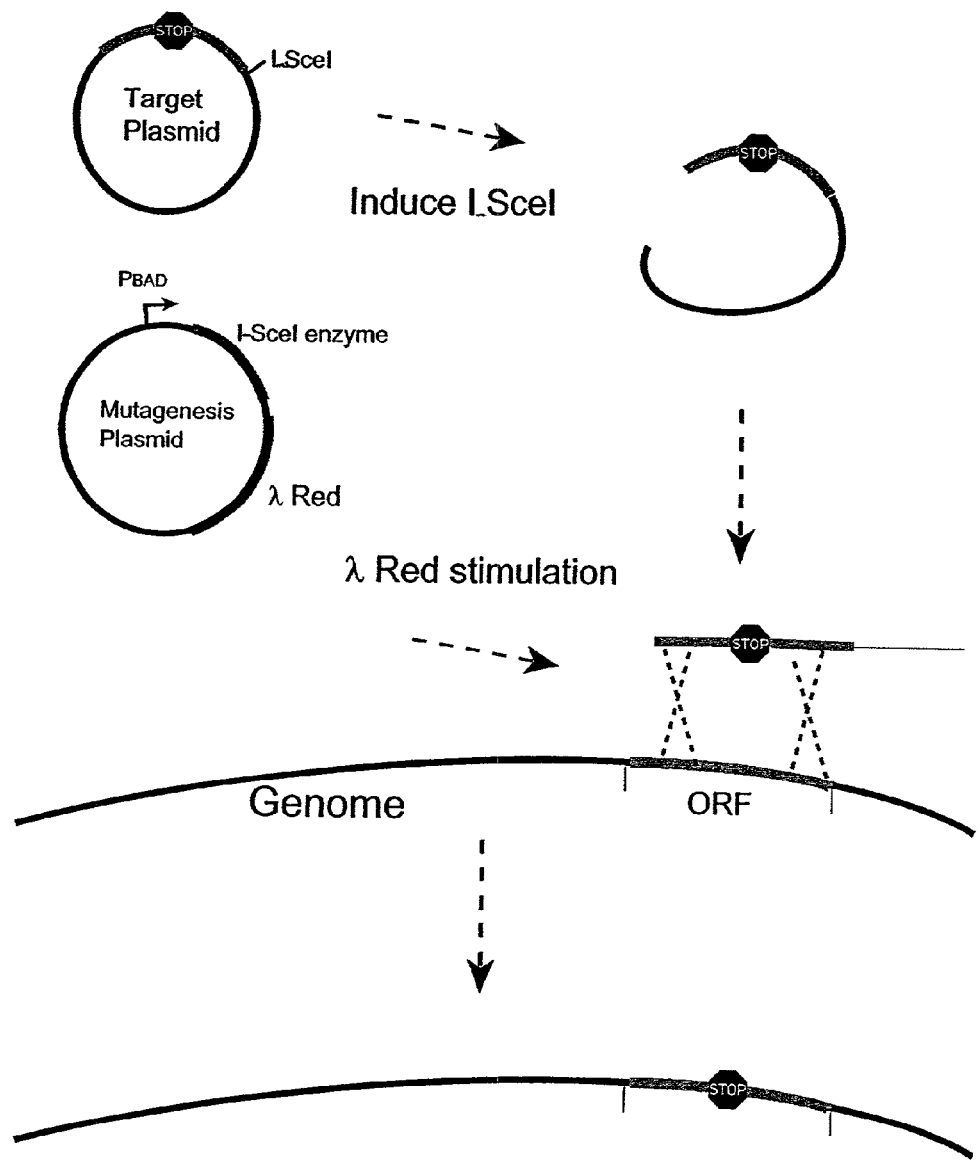
FIG. 3 illustrates a specific example of another linear DNA-based method of the present invention.
Figure 4:
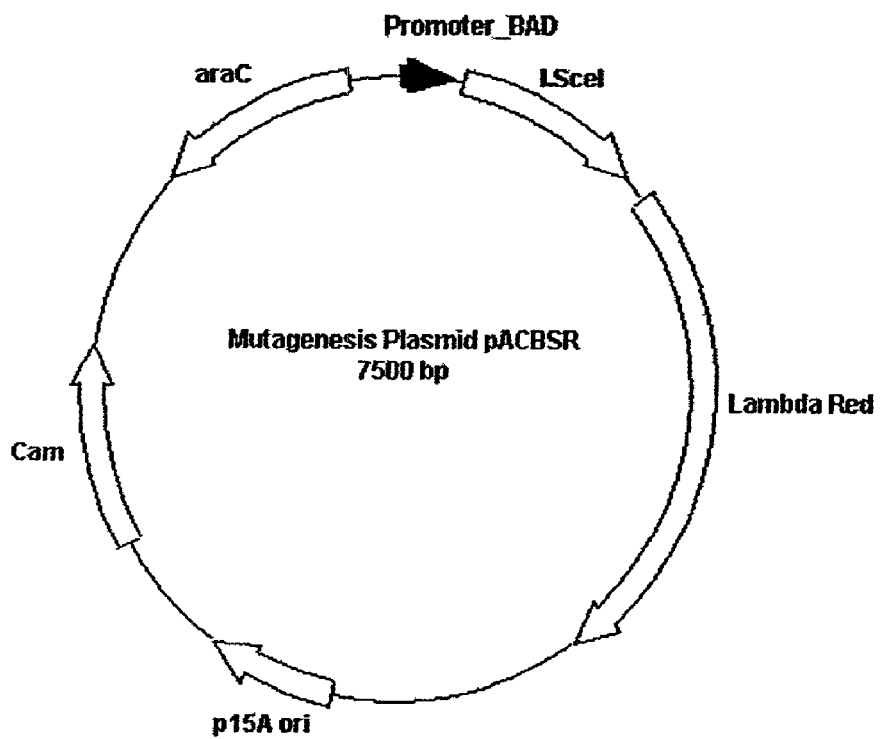
FIG. 4 shows a mutagenesis plasmid that can be used in the linear DNA-based method illustrated in FIG. 3.

As a specific example, FIGS. 3 and 4 illustrates using this method for introducing an Amber stop codon in the middle of a gene. As a first step, a DNA fragment with the desired modifications located near the middle of the gene or chromosomal region is produced. A sequence-specific nuclease I-SceI recognition site is introduced at one side of the DNA fragment. This can be easily accomplished by including the sequence in the 5' end of PCR primers used to amplify the DNA fragment. Longer DNA fragments (500–5,000 nucleotides) generally work the best.

The DNA fragment is cloned into a multi-copy target plasmid vector such as pUC 19 (GenBank accession No. M77789). Since this target vector is used along with a mutagenesis vector as described below, the target vector is engineered to be compatible with p15A origin plasmids (pACYC184-derived (GenBank accession No. X06403) and has a drug resistance marker other than chloramphenicol. These restrictions can be easily avoided by using an alternate mutagenesis plasmid.

As illustrated in FIG. 4, the mutagenesis plasmid used in this example contains the sequence-specific nuclease I-SceI and the lambda red genes exo, beta and gam under control of the P-BAD promoter. The plasmid also contains p15Aori and chloramphenicol resistance gene.

The target and the mutagenesis plasmids are transformed into a recA positive *E. coli*. The bacteria are selected for resistance to chloramphenicol and the resistance carried on the target plasmid. A single colony is then picked and cultured at 37° C. for about 7.0 hours in 1 ml of Rich Defined Media (Neidhardt et al., *J. Bacteriol.* 119:736–47, which is hereby incorporated by reference in its entirety) containing 0.2% arabinose and chloramphenicol. A series of dilutions (for example, 1:1,000, 1:10,000 and so on) of cultures is then plated on a non-selective medium such as LB. Next, the colonies are screened for desired mutations. If a growth phenotype is known, the screening can be done by patching on appropriate media. Otherwise, the screening is done with colony PCR followed by restriction digestion and electrophoresis or by sequencing.

Suicide Plasmid-Based Method

The suicide plasmid-based method described here can be used for both scarless gene deletion and gene replacement. The basic element of the method involves a plasmid vector named Interlock plasmid that contains and antibiotic resistance gene and a replication origin under the control of a promoter. The Interlock plasmid also contains one or more sites at which a DNA insert can be inserted. When the method is used for scarless deletion, the DNA insert includes two DNA sequences located right next to each other, oriented similarly, one of which is identical to a sequence that flanks one end of a bacterial genome region to be deleted and the other of which is identical to a sequence that flanks the other end of the bacterial genome region. When the method is used for gene replacement, the DNA insert includes a sequence that will replace a segment of a bacterial genome. When the promoter that controls the origin of replication is turned off, the replication of the plasmid is shut down and the antibiotic pressure can be used to select for chromosomal integrations. After chromosomal integration, the promoter that controls the replication origin from the plasmid can be turned on and the only bacteria that can survive are those that a recombination event has occurred to eliminate said origin of replication, its promoter or both. When the DNA insert is for making scarless deletion, the majority of the recombination event will result in bacteria that either have the desired scarless deletion or the same genome before any integration. When the DNA insert is for gene replacement, the majority of the recombination event will result in bacteria that either have the desired replacement or the same genome before any integration. A screening step can then be performed to identify those bacteria with desired modifications in the genome.

A variation of the above method involves the same Interlock plasmid except that the plasmid also contains a sequence-specific nuclease recognition site that is absent in the bacterial genome. After chromosomal integration, instead of activating the origin of replication control promoter to select for recombination events, the bacteria are engineered to express the sequence-specific nuclease to cut the bacterial genome and select for recombination events.

The suicide plasmid-based method can also be used repeatedly in a similar fashion as the novel liner DNA-based methods described above to generate a series of deletions on a bacterial genome.

FIG. 6 shows plasmid embodiments that can be used in the suicide plasmid-based method. pIL1 is an Interlock plasmid and pBAD-Sce-1 is a plasmid for expressing a sequence-specific nulcease I-SceI. pIL4 is a combination of both. The tet promoter used in pIL1 and pIL4 is tightly regulated and thus has advantages over other control mechanisms such as a temperature sensitive element which is more leaky. An example of using pIL4 for gene replacement is shown in FIG. 5A-C to illustrate the suicide plasmid-based method of the present invention. FIG. 5A shows that the insertion of a DNA insert into pIL4 and integration of pIL4 into the bacterial genome. With heat activated chlorotetracycline (CTC), tet repressor is inactive, the O and P promoter is functional, and the plasmid replicates. After removing CTC, tet repressor binds the O and P promoter and the replication is blocked. Chloramphenicol resistance can be used to select for integrants. FIG. 5B shows using the induction of the ectopic origin to select for homologous recombination and two possible outcomes of the homologous recombination. FIG. 5C shows the alternative way of selecting for homologous recombination and the two possible outcomes of the recombination. This alternative way involves inducing I-SceI expression to generate double-strand break.

Two specific embodiments of the suicide plasmid-based method are described below as protocol 1 and protocol 2. Either pIL1 or pIL4 can be used for protocol 1, and pIL1 in combination with pBAD-Sce-1 can be used for protocol 2. One of ordinary skill in the art can also adapt protocol 2 for using pIL4 alone.

Protocol 1 (Counterselection with Lambda Origin):
1. Generate the desired genomic modification as a linear DNA fragment. In the case of making an Amber mutant, the modification can be made by megaprimer PCR. To make a deletion in the genome, a fusion of the desired endpoints of the deletion should be used. The ends of the DNA fragment should be phosphorylated for cloning.
2. Create a blunt cloning site by digesting the pIL4 vector (FIGS. 5A and 6) with the restriction enzyme SrfI. Dephosphorylate the vector.
3. Perform a blunt ligation of the desired modification and the pIL4 vector.
4. (Note: this step is potentially dispensable in high throughput implementation.) Transform the ligation into a cloning strain of E coli (such as JS5). Outgrow the transformation for 1 hour in LB+1 ug/ml cTc (cTc—chlortetracycline freshly autoclaved in LB media. A stock of 100 µg/ml is autoclaved for 20 minutes and then stored in the dark at 4° C. It can be used for up to 5 days. Alternately, a solution of 2 ng/ml of anhydrotetracycline can be substituted). Then plate on LB+Chloramphenicol (Cam 25 µg/ml)+cTc (1 µg/ml), and grow overnight at 37° C. Grow colonies in equivalent media and prepare plasmid miniprep DNA. Analyze by gel electrophoresis and select a clone with an insert.
5. Transform the verified plasmid into a recA positive strain of E coil (such as MG1655). Outgrow for 1 hour in LB+1 µg/ml cTc. Plate a portion of the outgrowth on plates containing Cam and 1 µg/ml cTc. Grow overnight at 37° C.
6. Pick a colony into 1 ml LB and plate 10 µl on a Cam plate. Grow overnight at 37° C.
7. Streak a colony on a Cam plate to be sure that every cell present contains the integrated plasmid. Grow overnight at 37° C.
8. Pick a colony into 1 ml LB and plate 100 µl of a 1:100 dilution on plates containing 5 µg/ml cTc. Grow overnight at 37° C.
9. (Screen for mutant) Only a fraction of the counterselected colonies will contain the desired modification and the others will be reversions to wt. The proportion of mutant to revertant will depend on the location of the modification in the cloned fragment. Some kind of screen must be performed to identify the desired mutant. For the production of Amber mutants, the gene in question can be amplified by PCR and digested with BfaI restriction enzyme (BfaI cuts Amber codons that are preceded by a 'C').

Protocol 2 (High Thruput Counterselection with I.SceI):
1-4 Same as protocol 1.
5. Co-transform the insert-carrying Interlock plasmid and pBAD-SceI into a recA positive strain of E coli (such as MG 1655). Outgrow for 1 hour in LB+1 ug/ml cTc. (Alternatively, the insert-carrying Interlock plasmid can be transformed on it's own into competent cells already carrying pBAD-SceI).
6. Add Chloramphenicol to 25 µg/ml and Kanamycin to 50 µg/ml. Grow for 1–2 hours at 37° C. with shaking.
7. Pellet the cells in a microcentrifuge for 30 seconds. Remove the media supernatant.
8. (Integration step) Resuspend the cells in 1 ml LB+Chloramphenicol (25 µg/ml)+Kanamycin (50 µg/ml) +Glucose (0.2%) and grow overnight at 37° C., shaking.
9. Dilute the overnight culture 1:10,000 in the same media and grow an additional 16–24 hours at 37° C.
10. (Counter selection step) Dilute 10 µl of the culture into 1 ml 1×M9 minimal salts (to minimize growth rate). Split this into two tubes of 0.5 ml each. To one add Arabinose to 0.2% and to the other add Glucose to 0.2% (to serve as a negative control). Grow 1–2 hours at 37° C. with shaking.
11. Plate 10 µl of the Arabinose tube onto LB+Kanamycin (50 µg/ml)+Arabinose (0.2%) and 10 µl of the Glucose tube onto LB+Chloramphenicol (25 µg/ml)+Kanamycin (50 µg/ml)+Glucose (0.2%). Grow overnight at 37° C.
12. (Screen for mutant) Perform step 9 of the primary protocol.

The above disclosure generally describes the present invention. The invention will be more fully understood upon consideration of the following examples which are provided herein for purposes of illustration only and are not intended to limit the scope of the invention.

EXAMPLES

Plasmids

The plasmid used for PCR construction of the artificial inserted DNA sequence was designated pSG76-CS (GenBank Accession No. AF402780), which was derived from pSG76-C (Posfai, G. et al., *J. Bacteriol.* 179: 4426–4428 (1997)) by inserting a second I-SceI site. The second I-SceI site was obtained by the PCR-mediated insertion of a second I-SceI recognition site into pSG76-C, downstream of the NotI site. The two I-SceI sites are in opposite direction.

The pBADαβγ plasmid was used for enhancing recombination of linear DNA-fragments into the genome. This plasmid was described in Muyrers, J. P. P. et al., *Nucl. Acids Res.* 27:1555–1557 (1999).

The PKSUC1 plasmid (GenBank Accession No. AF402779), for expressing I-SceI, was derived from pSG76-K (Posfai, G. et al., *J. Bacteriol.* 179: 4426–4428 (1997)) and pUC19RP12 (Posfai, G. et al., *Nucl. Acids Res.* 27: 4409–4415 (1999)). The XbaI-NotI fragment (carries the Kan gene; the NotI end was blunted by Klenow polymerase) of pSG76-K was ligated to the XbaI-DraI fragment (carries the I-SceI gene and the pUC ori) of pUC19RP12.

The pKSUC5 plasmid for tetracycline-regulated expression of I-SceI was derived from pFT-K (Posfai, G. et al., *J.*

*Bacteriol.* 179: 4426–4428 (1997)) and pKSUC1. The large XbaI-NcoI fragment of pKSUC1 was ligated to the XbaI-NcoI fragment of pFT-K carrying the tet repressor.

The PKD46 plasmid for enhancing recombination of linear DNA-fragments into the genome was described in Datsenko, K. A. et al., *Proc. Natl. Acad. Sci.* 97:6640–6649 (2000).

The plasmid pSTKST (GenBank Accession No. AF406953) is a low copy number $Kan^R$ plasmid for chlortetracycline-regulated expression of I-SceI, derived from pFT-K (Posfai, G. et al., *J. Bacteriol.* 179: 4426–4428 (1997)) and pUC19RP12 (Posfai, G. et al., *Nucl. Acids Res.* 27: 4409–4415 (1999)). The XbaI-PstI fragment from pUC19RP12, carrying the I-SceI gene, was ligated to the large XbaI-PstI fragment of pFT-K. This plasmid expresses I-SceI when induced by chlortetracycline. Replication of the plasmid is temperature-sensitive (Posfai, G. et al., *J. Bacteriol.* 179: 4426–4428 (1997)).

The plasmid pSTAST, a low copy number $Ap^R$ plasmid for chlortetracycline-regulated expression of I-SceI, was derived from pFT-A (Posfai, G. et al., *J. Bacteriol.* 179: 4426–4428 (1997)) and pUC19RP12 (Posfai, G. et al., *Nucl. Acids Res.* 27: 4409–4415 (1999)). The XbaI-PstI fragment from pUC19RP12, carrying the I-SceI gene, was ligated to the large XbaI-PstI fragment of pFT-A. This plasmid expresses I-SceI when induced by chlortetracycline. Replication of the plasmid is temperature-sensitive (Posfai, G. et al., *J Bacteriol.* 179: 4426–4428 (1997)).

Procedure 1

This describes the process used to repeatedly make deletions from the genome of *E. coli* K12. This procedure is a scarless deletion method. The procedure begins with the construction of a linear target fragment by PCR. This was done by mixing 20 pmol of primer A with 20 pmol primer B, and performing PCR in a total volume of 50 $\mu$l. The cycle parameters used were 15×(94° C. 40 sec/57° C. or lower (depending on the overlap of A and B) 40 sec/72° C. 15 sec). The 1 $\mu$l of the PCR mix above were taken, added to 20 pmol of primers A and C each, add 50 ng of pSG76-CS and perform PCR in a volume of 2×50 $\mu$l (use 50-$\mu$l tubes, and two tubes are combined to have more DNA). The cycle parameters used were 28×(94° C. 40 sec/57° C. 40 sec/72° C. 80 sec). To purify the PCR mix from the above step, Promega Wizard PCR purification kit was used. The resulting DNA fragment was suspended in 20 $\mu$l water.

Next was the replacement of a genomic region by insertion of the artificial DNA-fragment. This was done by taking the target cell carrying pBADαβγ and preparing electrocompetent cells as described (Posfai, G. et al., *Nucl. Acids Res.* 27: 4409–4415 (1999)), except that 0.1% arabinose was added to the culture 0.25–1 hour before harvesting the cells. 4 $\mu$l of DNA fragments (100–200 ng) were electroporated into 40 $\mu$l of electrocompetent cells. The cells were plated on Cam plates (25 $\mu$g cam/ml) and incubated at 37° C. The usual result was to obtain a total of 10 to several hundred colonies after overnight incubation. A few colonies were checked for correct site insertion of the fragment by PCR using primers D and E.

Next was the deletion of the inserted sequences. This was done by preparing competent cells derived from a selected colony from above by the $CaCl_2$ method (Sambrook, J. et al., Molecular Cloning: A Laboratory Manual. Cold Spring Harbor Laboratory Press, Cold Spring Harbor, N.Y. (1989)). The plasmid pKSUC1 (~100 ng) was transformed into the cells by standard procedures (Sambrook, J. et al., Molecular Cloning: A Laboratory Manual. Cold Spring Harbor Laboratory Press, Cold Spring Harbor, N.Y. (1989)). The cells were plated on Kan plates and incubated at 37° C. (pKSUC1 and pBADαβγ are incompatible, thus selection on Kan eliminates pBADαβγ from the cells). The colonies were checked for correct deletion by PCR using primers D and E. A colony was selected carrying the correct deletion. At this point, the cells carried pKSUC1. The next step is to delete this plasmid.

This deletion is done through the replacement of pKSUC1 with pBADαβγ. A colony from the prior step was selected, grown in LB at 37° C. under nonselective conditions, reinoculating the cells into fresh medium 2–3 times. Competent cells were prepared for either chemical transformation or electroporation. The plasmid pBADαβγ y (100–200 ng) was transformed into the competent cells which were plated on Amp plates. A colony which was Kan sensitive/Amp resistant was selected by toothpicking a hundred colonies on Kan and Amp plates.

The selected colony can be used in a next round of deletion by using a new targeting fragment and repeating the steps above. If no more deletions are needed, growing the cells under nonselective conditions (no Amp is added) results in the spontaneous loss of pBADαβγ from a large fraction of the cells.

Procedure 2

This procedure is similar to procedure 1, but pKSUC1 is replaced by pSTKST. This plasmid is compatible with pBADαβγ, has a temperature-sensitive replicon, and expression of I-SceI requires induction by chlortetracyclin (CTC). The advantage is that elimination of pSTKST from the cell is easily accomplished by growing the culture at 42° C.

Construction of a linear targeting fragment by PCR and replacement of a genomic region by insertion of the fragment are done as described in Procedure 1.

To delete the inserted sequences competent cells are prepared from a culture derived from a selected colony harboring the right insertion. Cells are transformed by pSTKST, plated on Kan+Cam plates and incubated at 30° C. A colony from this plate is inoculated into 10 ml of LB+Kan supplemented with heat-treated inducer cTc (25 $\mu$g/ml final concentration) and grown at 30° C. for 24 hours. This step serves induction of the expression of I-SceI. Dilutions of the culture are then spread on LB+Kan plates and incubated overnight at 30° C. 6–12 colonies were checked for correct deletion by PCR using primers D and E. A colony was selected carrying the correct deletion.

To eliminate the helper plasmids from the cell, the culture is grown at 42° C. in LB (no antibiotics added).

Procedure 3

Since pBADαβγ and pSTKST carry compatible replicons, repeated transformations of the plasmids are not required when consecutive deletions are made in the same host. The two plasmids are maintained in the host cell throughout consecutive deletion constructions by antibiotic selection (Kan+Amp). Recombinase and specific nuclease functions are induced only when needed. Since replication of pSTKST is temperature-sensitive, cells must be grown at 30° C.

The procedure is identical to Procedure 2, except that pBADαβγ and pSTKST are transformed into the cell only once, and until maintenance of both plasmids in the cell is desired, the culture is grown at 30° C., and Amp+Kan are included in the medium. Note: Sometimes we experienced difficulties in growing the cells at 30° C. in the presence of two (Amp+Kan) or three (Amp+Kan+Cam) antibiotics.

Procedure 4

This is the preferred procedure when several consecutive deletions are to be made in the same cell. Insertions (recombination of linear fragments into the genome of a host cell carrying pBADαβγ) are made in parallel, creating a series of recombinant cells, each carrying a single insertion. These insertions are then transferred one by one by P1 transduction into the cell carrying pSTKST and harboring all previous deletions. Removal of all foreign sequences is done in this final host by inducing pSTKST. Compared to the previous methods, the main difference is that the insertion step and removal of the inserted sequences are done in separate cells. Since insertions are made in parallel, the construction of consecutive deletions is faster. Another advantage is that cells are transformed by the plasmids only at the beginning of the first deletion construction.

Technically the procedure is identical to Procedure 2, except that individual insertions are transferred by P1 transduction to the deletion strain already harboring pSTKST. After each PI transduction step, I-SceI expression is induced to remove the inserted sequences.

Results

Twelve consecutive genomic deletions have been made from E. coli strain K12 MG1655. The twelve deleted regions were selected for deletion, in part, as a result of comparison of the genomic DNA sequences of E. coli strain O157:H7 EDL933 and strain K-12 MG1655. The deletions are listed on Table 1 below. The sequence numbering is taken from the published K12 sequence.

The first deletion MD1 was made using the method described in Posfai, G. et al., Nucl. Acids Res. 27: 4409–4415 (1999). Using this method for creating MD1 deletion left a 114-bp pSG76-CS vector sequence, including a FRT site, in the chromosome at the site of deletion. MD2 through MD6 deletions were made using Procedure 1 described above. Deletions MD7 through MD12 were created using a combination of Procedure 4 and Procedure 1 or 2. Strain designations and genomic coordinates of each new deletion were: MD1 263080–324632; MD2 1398351–1480278; MD3 2556711–2563500; MD4 2754180–278970; MD5 2064327–2078613; MD6 3451565–3467490; MD7 2464565–2474198; MD8 1625542–1650865; MD9 4494243–4547279; MD10 3108697–3134392; MD11 1196360–1222299; MD12 564278–585331.

A total of 378,180 base pairs, which is approximately 8.1% of the native K12 MG1655 E. coli genome, was removed at this stage. Removing these regions from the genome did not affect bacterial survival or bacterial growth.

Table 2 below lists other segments, genes and regions of the E. coli genome that were identified as candidates for further deletions. The seqments wer also successfully removed from the genome of the bacteria. Again, these deletions were made without any apparent deleterious effect on the usefulness of the bacteria for laboratory and industrial use. Again the sequence designations are taken from the published K12 sequence. The two sets of deletions totaled about 14% of the original bacterial genome. Further deletions are, of course, possible.

In Procedure 1, efficiency of the insertion of the linear fragment varied with the particular genomic locus. Correct-site insertion occurred in 1–100% (normally 20–100%) of the colonies. Flanking homologies in the range of 42 to 74 bp were used. Longer homologies give better insertion efficiencies. Correct-site excision between the duplicated sequences occurred in 1–100% (normally 10–100%) of the colonies and depended on the length of the duplicated region. Longer duplications are usually more effective. Length of the duplicated sequences was in the range of 42 to 50 bp. Variations in the efficiencies of insertion and excision existed between seemingly identically repeated experiments and are not fully understood yet.

Procedure 3 was tested by re-creating deletion MD2. Correct-site insertion of the linear DNA-fragment occurred in 6.6% of the colonies. Deletion of the inserted sequence was very efficient. Twenty-five resulting colonies were replica plated on Cam+Amp+Kan and Amp+Kan plates, and 19 of them proved to be Cam sensitive. Five of these colonies were then tested by PCR, and all 5 showed the predicted loss of the inserted sequence.

In the above description, the present invention is described in connection with specific examples. It will be understood that the present invention is not limited to these examples, but rather is to be construed to be of spirit and scope defined by the appended claims.

TABLE 1

FIRST COMPLETED DELETIONS

| Deletion | Endpoints [a] | Size (bp) | Description [b] |
|---|---|---|---|
| MD1 | 263080, 324632 | 61553 | b0246–b0310; includes K-islands #16, 17, 18, CP4-6, eaeH |
| MD2 | 1398351, 1480278 | 81928 | b1336–b1411; includes K-island #83, Rac |
| MD3 | 2556711, 2563500 | 6790 | b2441–b2450; includes K-island #128, CP-Eut |
| MD4 | 2754180, 2789270 | 35091 | b2622–b2660; includes K-island #137, CP4-57, ileY |
| MD5 | 2064327, 2078613 | 14287 | b1994–b2008; includes K-islands #94, 95, 96, CP4-44 |
| MD6 | 3451565, 3467490 | 15926 | b3323–b3338; includes K-islands #164, 165 |
| MD7 | 2464565, 2474198 | 9634 | b2349–b2363; includes K-island #121 |
| MD8 | 1625542, 1650785 | 25244 | b1539–b1579; includes K-island #77, Qin |
| MD9 | 4494243, 4547279 | 53037 | b4271–b4320; includes K-island #225, fec operon, fim operon |
| MD10 | 3108697, 3134392 | 25696 | b2968–b2987; includes K-island #153, glc operon |
| MD11 | 1196360, 1222299 | 25940 | b1137–b1172; includes K-island #71, e14 |
| MD12 | 564278, 585331 | 21054 | b0538–b0565; includes K-island #37, DLP12 |

TABLE 2

SECOND SET OF COMPLETED DELETIONS

IS186 deletions (3)

| | |
|---|---|
| keep dnaJ | 14168, 15298 (+) |
| *delete GP1 | 15388, 20563 IS186, gef, nhaAR, IS1 |
| [IS186 | 15388, 16730] |
| [IS1 | 19796, 20563] |

TABLE 2-continued

SECOND SET OF COMPLETED DELETIONS

| | |
|---|---|
| keep rpsT | 20815, 21078 (−) |
| keep pheP | 601182, 602558 (+) |
| *delete GP2 | 602639, 608573 ybdG, nfnB, ubdF, ybdJ, ybdK, IS186 |
| {IS186 | 607231, 608573] |
| keep entD | 608682, 609311 (−) |
| keep glk | 2506481, 2507446 (−) |
| *delete GP3 | 2507650, 2515969 b2389, b2390, b2391, b2392, nupC, IS186, yfeA |
| [IS186 | 2512294, 2513636] |
| keep alaX | 2516061, 2516136 (−) |
| IS2 deletions | |
| (3 not already deleted) | |
| Keep yaiN | 378830, 379126 (−) |
| *delete GP4 | 379293, 387870 yaiO, b0359, IS2, b0362, yaiP, yaiS, tauABCD |
| [IS2 | 380484, 381814] |
| keep hemB | 387977, 388984 (−) |
| *delete GP5 | 389121, 399029 b0370, yaiT, IS3, yaiU, yaiV, ampH, sbmA, yaiw, yaiY, yaiZ |
| [IS3 | 390933, 392190] |
| keep ddlA | 399053, 400147 (−) |
| keep ygeK | 2992482, 2992928 (−) |
| *delete GP6 | 2992959, 2996892 b2856, b2857, b2858, b2859, IS2, b2862, b2863 |
| [IS2 | 2994383, 2995713] |
| keep glyU | 2997006, 2997079 (−) |
| keep ribB | 3181829, 3182482 (−) |
| *delete GP7 | 3182796, 3189712 b3042, ygiL, IS2, yqiGHI (fimbral locus) |
| [IS2 | 3184112, 3185442] |
| keep glgS | 3189755, 3189955 (−) |
| IS5 deletions | |
| (6 not already deleted) | |
| keep ybeJ | 686062, 686970 (−) |
| *delete GP8 | 687074, 688268 IS5 |
| keep lnt | 688566, 690104 (−) |
| keep tpx | 1386329, 1386835 (−) |
| *delete GP9 | 1386912, 1396646 ycjG, ycjI, ycjY, ycgZ, mppA, ynaI, IS5, ynaJ, ydaA |
| [IS5 | 1394680, 1395262] |
| keep fnr | 1396798, 1397550 (−) |
| keep gnd | 2097884, 2099290 (−) |
| *delete GP10 | 2099418, 2135739 IS5 plus entire O Antigen and Colanic Acid clusters |
| [IS5 | 2099771, 2100965] |
| keep yegH | 2135858, 2137507 (+) |
| keep proL | 2284231, 2284307 (+) |
| *delete GP11 | 2284410, 2288200 yejO and IS5 |
| [IS5 | 2286939, 22881333] |
| keep narP | 2288520, 2289167 (+) |
| keep gltF | 3358811, 3359575 (+) |
| *delete GP12 | 3359747, 3365277 IS5 plus yhcADEF (K-island) |
| [IS5 | 3363191, 3364385] |
| keep yhcG | 3365462, 3366589 (+) |
| keep arsC | 3647867, 3648292 (+) |
| *delete GP13 | 3648921, 3651343 yhis and IS5 |
| (IS5 | 3640666, 3650860] |
| keep slp | 3651558, 3652157 (+) |
| flagella | |
| Region I | |
| keep mviN | 1127062, 1128597 (+) |
| *delete GP14 | 1128637, 1140209 flgAMN flgBCDEFGHIJKL |
| keep rne | 1140405, 1143590 (−) |
| Region II | |
| keep yecT | 1959975, 1960484 (+) |
| *delete GP15 | 1960605, 1977294 flh, che, mot, tap, tar, IS1 |
| keep yecG | 1977777, 1978205 (+) |
| Regions IIIa and IIIb try deleting both in one action | |
| keep sdiA | 1994133, 1994855 (−) |
| *delete Gp16 | 1995085, 2021700 fli, plus amyA, yec and yed ORFs |
| keep rcsA | 2021990, 2022613 (+) |
| hsd region | |
| keep uxuR | 4552145, 4552918 (+) |
| *delete GP17 | 4553059, 4594581 yji ORFS, plus mcrBCD, hsdRMS, mrr, tsr |
| keep mdoB | 4594719, 4596971 (−) |
| Rhs elements | |
| keep ybbP | 519640, 522054 (+) |
| *delete GP18 | 522062, 529348 RhsD element & associated ORFs |
| keep ybbB | 529356, 530450 (−) |
| keep ybfA | 728357, 728563 (+) |
| *delete GP19 | 728616, 738185 RhsC element & associated ORFs |
| keep ybgA | 738224, 738733 (+) |
| keep yncH | 1524964, 1525176 (+) |
| *delete GP20 | 1525914, 1531648 RhsE element & associated ORFs |
| keep nhoA | 1532048, 1532893 (+) |
| keep nikR | 3616219, 361662 (+) |
| *delete GP21 | 3616623, 3623309 RhsB element & associated ORFs # may need to leave something here to separate converging ORFs? |
| keep yhhJ | 3623310, 3624437 (−) |
| keep yibF | 3758974, 3759582 (−) |
| *delete GP22 | 3759620, 3767868 RhsA element & associated ORFs |
| keep yibH | 3767870, 3769006 (−) |
| the rest of the IS elements | |
| keep appA | 1039840, 1041138 (+) |
| *delete GP23 | 1041253, 1049768 yccZYC (EPS), ymcDCBA (EPS?), IS1 |
| [IS1 | 1049001, 1049068] |
| keep cspH | 1050186, 1050398 (−) |
| keep phoH | 1084215, 1085279 (+) |
| *delete GP24 | 1085329, 1096603 ycdSRQPT (hms homologues), IS3, ymdE, ycdU |
| [IS3 | 1093468, 1094725] |
| keep serX | 1096788, 1096875 (−) |
| keep baeR | 2162298, 216302 (+) |
| *delete GP25 | 2163172, 2175230 P2 remnant, IS3, gat operon |
| [IS3 | 2168193, 2169450] |
| keep fbaB | 2175532, 2176656 (−) |
| keep yhhX | 3577399, 3578436 (−) |
| *delete GP26 | 3578769, 3582674 yhhYZ, IS1, yrhAB |
| [IS1 | 3581059, 3581826] |
| keep ggt | 3582712, 3584454 (−) |
| keep cspA | 3717678, 3717890 (+) |
| *delete GP27 | 3718262, 3719704 IS150 |
| [IS150 | 3718262, 3719704] |
| keep glyS | 3719957, 3722026 (−) |

We claim:

1. An *E. coli* bacterium having a genome that is genetically engineered to be at least 5% smaller than the genome of its native parent strain.

2. The bacterium of claim 1, wherein its genome is genetically engineered to be at least 8% smaller than the genome of its native parent strain and wherein there are no scars in the genome resulting from the deletions.

3. The bacterium of claim 1, wherein its genome is genetically engineered to be at least 14% smaller than the genome of its native parent strain.

4. The bacterium of claim 1, wherein the genome of the bacterium is genetically engineered to delete from the genome of the bacteria DNA selected from the group consisting of a flagella gene, a restriction modification system gene, a lipopolysaceharide surface synthetic gene, an insertion sequence element, a rhs element, a non-transcribed region in the genome of the native parent strain and a gene or other DNA sequence that is not present in both of any two bacteria strains of the same species of the native parent strain.

5. An *E. coli* bacterium having a genome that is genetically engineered to be smaller than 4.27 Mb.

6. A strain of *E. coli* bacteria having a genome is genetically altered to be smaller than 4.00 Mb.

* * * * *

UNITED STATES PATENT AND TRADEMARK OFFICE
CERTIFICATE OF CORRECTION

PATENT NO. : 6,989,265 B2  Page 1 of 1
APPLICATION NO. : 10/057582
DATED : July 3, 2006
INVENTOR(S) : Blattner et al.

It is certified that error appears in the above-identified patent and that said Letters Patent is hereby corrected as shown below:

In claim 4, column 21, line 5, delete "lipopolysaceharide" and insert --lipopolysaccharide-- therefor.

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,265 B2 Page 1 of 1
APPLICATION NO. : 10/057582
DATED : January 24, 2006
INVENTOR(S) : Blattner et al.

It is certified that error appears in the above-identified patent and that said Letters Patent is hereby corrected as shown below:

In claim 4, column 21, line 5, delete "lipopolysaceharide" and insert --lipopolysaccharide-- therefor.

This certificate supersedes Certificate of Correction issued August 15, 2006.

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

PATENT NO. : 6,989,265 B2
APPLICATION NO. : 10/057582
DATED : January 24, 2006
INVENTOR(S) : Frederick R. Blattner et al.

Page 1 of 1

It is certified that error appears in the above-identified patent and that said Letters Patent is hereby corrected as shown below:

In the Specification

Column 1, Lines 6-10:
Delete the phrase:
"This invention was made with United States government support awarded by the following agency: NIH GM35682 The United States has certain rights in this invention."

And replace with:
--This invention was made with government support under GM035682 awarded by the National Institutes of Health. The government has certain rights in the invention.--.

Signed and Sealed this
Twenty-second Day of December, 2020

Andrei Iancu
*Director of the United States Patent and Trademark Office*